(12) United States Patent
Hirota et al.

(10) Patent No.: US 8,287,464 B2
(45) Date of Patent: Oct. 16, 2012

(54) METAL NEEDLE USABLE IN ECHO IMAGING

(75) Inventors: Hiroshi Hirota, Nasu-Shiobara (JP);
Yoshiharu Iwase, Osaka (JP)

(73) Assignee: Nipro Corporation, Osaka-shi (JP)

( * ) Notice: Subject to any disclaimer, the term of this patent is extended or adjusted under 35 U.S.C. 154(b) by 227 days.

(21) Appl. No.: 12/516,303

(22) PCT Filed: Mar. 31, 2008

(86) PCT No.: PCT/JP2008/056830
§ 371 (c)(1),
(2), (4) Date: May 26, 2009

(87) PCT Pub. No.: WO2008/120824
PCT Pub. Date: Oct. 9, 2008

(65) Prior Publication Data
US 2010/0069789 A1    Mar. 18, 2010

(30) Foreign Application Priority Data
Mar. 30, 2007    (JP) ................................ 2007-093359

(51) Int. Cl.
*A61B 6/00* (2006.01)
*A61B 8/00* (2006.01)
*A61B 10/00* (2006.01)
(52) U.S. Cl. ......................... 600/562; 600/431; 600/437
(58) Field of Classification Search .................. 600/431, 600/562–568, 437; 29/592, 896.1
See application file for complete search history.

(56) References Cited

U.S. PATENT DOCUMENTS

| 4,146,022 | A  | * | 3/1979  | Johnson et al. ................ 606/74  |
| 4,647,480 | A  |   | 3/1987  | Ahmed                                  |
| 5,344,640 | A  |   | 9/1994  | Deutsch et al.                         |
| 6,474,350 | B1 |   | 11/2002 | Mizuta                                 |
| 6,610,016 | B1 |   | 8/2003  | Violante et al.                        |
| 6,749,554 | B1 |   | 6/2004  | Snow et al.                            |
| 2003/0171777 | A1 | * | 9/2003  | Roby et al. .................... 606/222 |
| 2005/0038358 | A1 | * | 2/2005  | Furukawa ..................... 600/585 |
| 2005/0143656 | A1 |   | 6/2005  | Burbank et al.                         |
| 2006/0069405 | A1 |   | 3/2006  | Schaeffer et al.                       |
| 2007/0255140 | A1 |   | 11/2007 | Violante et al.                        |
| 2008/0194930 | A1 | * | 8/2008  | Harris et al. .................. 600/310 |

(Continued)

FOREIGN PATENT DOCUMENTS

JP          3228748 A    10/1991
(Continued)

*Primary Examiner* — Max Hindenburg
*Assistant Examiner* — Jonathan M Foreman
(74) *Attorney, Agent, or Firm* — The Webb Law Firm

(57) ABSTRACT

A metal needle is obtained by being dipped in a liquid selected from the group consisting of a strong acid solution of a metal, acetic acid, and butyl acetate, and then dried. Preferably, the strong acid solution of a metal to be used in the dipping treatment may be a nitric acid solution of a metal selected from the group consisting of a transition element, a lanthanoid, and an actinoid, for example, a nitric acid solution of a metal selected from the group consisting of palladium, gadolinium, germanium, beryllium, strontium, scandium, and samarium. The metal needle is a metal needle for insertion into the body that can be reliably imaged even when a general-purpose ultrasound imaging system is used, and thus is useful in confirming insertion of the needle into a blood vessel and arrival of the needle at an organ, and confirming the position of the needle when it is broken.

11 Claims, 4 Drawing Sheets

U.S. PATENT DOCUMENTS

2009/0137906 A1    5/2009    Maruyama et al.

FOREIGN PATENT DOCUMENTS

| | | |
|---|---|---|
| JP | 11230989 A | 8/1999 |
| JP | 2001190560 A | 7/2001 |
| JP | 2002040048 A | 2/2002 |
| JP | 2002537877 T | 11/2002 |
| JP | 2003126106 A | 5/2003 |
| JP | 2007503263 T | 2/2007 |
| WO | 2005020905 A2 | 3/2005 |
| WO | 2006034233 A1 | 3/2006 |
| WO | 2007013130 A1 | 2/2007 |

\* cited by examiner

METAL NEEDLE USABLE IN ECHO IMAGING

TECHNICAL FIELD

The present invention relates to a metal needle that can be imaged in echo imaging. More specifically, the present invention relates to the metal needle for insertion into the human and animal body.

BACKGROUND ART

During a procedure to retrieve an ovum from an ovary of a human or an animal, generally, a tissue collection needle is attached to an ultrasound probe, and the tissue collection needle is used to puncture the body so that the needle arrives at the ovary under ultrasound and echo imaging. According to the difference in the method of inserting the needle, ultrasound-guided ovum retrieval is classified into transvesical ovum retrieval using an abdominal probe, transvaginal ovum retrieval using an abdominal probe or a transvaginal probe, and transurethral ovum retrieval using an abdominal probe. Currently, the transvaginal method is most commonly adopted among the ultrasound-guided ovum retrieval techniques, because, for example, the puncture distance is short, which avoids injury to the skin, and local anesthesia is effective.

Ultrasound-guided ovum retrieval has been performed by repeating operations of puncturing a follicle with a single-needle type ultrasound needle, infusing lavage fluid into the follicle with a syringe, and then aspirating the follicle with another syringe to retrieve an ovum. However, in this method, the sharpened edge of the needle moves or the lavage fluid flows backward or leaks during the operation of exchanging one syringe for another syringe, and so there were disadvantages that it takes time to retrieve an ovum and also the yield of such ovum retrieval is low. Afterward, a double-lumen tissue collection needle including an outer hollow metal needle provided with a sharpened edge at the tip thereof and an inner hollow tube installed inside the outer needle has been developed so that it is ensured that the inner diameter of an ovum retrieval route is large enough to allow ova to pass through the route and the flow rate through a lavage route is also sufficient (Japanese Laid-Open Patent Publication Nos. 2001-190560 and 2003-126106).

Generally, not only such tissue collection needles but also needles that are to be inserted into the body while their position being confirmed by echography are provided with an echo guide that reflects ultrasound waves on the external surface near the tip portion of the needles. The echo guide may include, for example, a surface having microscopic asperities formed by grinding and slitting or sandblasting. The surface area on which the echo guide is formed is small so that the echo guide does not affect puncture and insertion of the needles. If a very high-precision ultrasound imaging system is used, needles can be imaged even without such an echo guide. However, only a portion of the echo guide can be imaged by a common general-purpose ultrasound imaging system. Accordingly, when a needle is fixed, the needle cannot be imaged in some cases depending on, for example, the relationship between the orientation of the needle and the scanning direction of an ultrasound probe. Therefore, it is considerably difficult to reliably know the position of a very fine needle tip by echography.

SUMMARY OF THE INVENTION

Disclosure of Invention

It is an object of the present invention to provide a metal needle for insertion into the body that can be reliably imaged even when a general-purpose ultrasound imaging system is used.

The present invention provides a metal needle that is obtained by being dipped in a liquid selected from the group consisting of a strong acid solution of a metal, acetic acid, and butyl acetate, and then dried.

In one embodiment, the strong acid solution of a metal is a nitric acid solution of a metal selected from the group consisting of a transition element, a lanthanoid, and an actinoid.

In a further embodiment, the strong acid solution of a metal is a nitric acid solution of a metal selected from the group consisting of palladium, gadolinium, germanium, beryllium, strontium, scandium, and samarium.

In one embodiment, the strong acid solution of a metal has a concentration of the metal of 980 to 1020 mg/L and a concentration of the strong acid of 0.08 to 1.1 mol/L.

In an embodiment, the metal needle is for tissue collection.

In one embodiment, the liquid is a standard stock solution for atomic absorption spectrometry.

According to the present invention, a metal needle that can be reliably imaged even with a general-purpose ultrasound imaging system is provided. Thus, the needle can be more reliably imaged using an existing system even without using a state-of-the-art ultrasound imaging system.

BEST MODE FOR CARRYING OUT THE INVENTION

Figure 1:
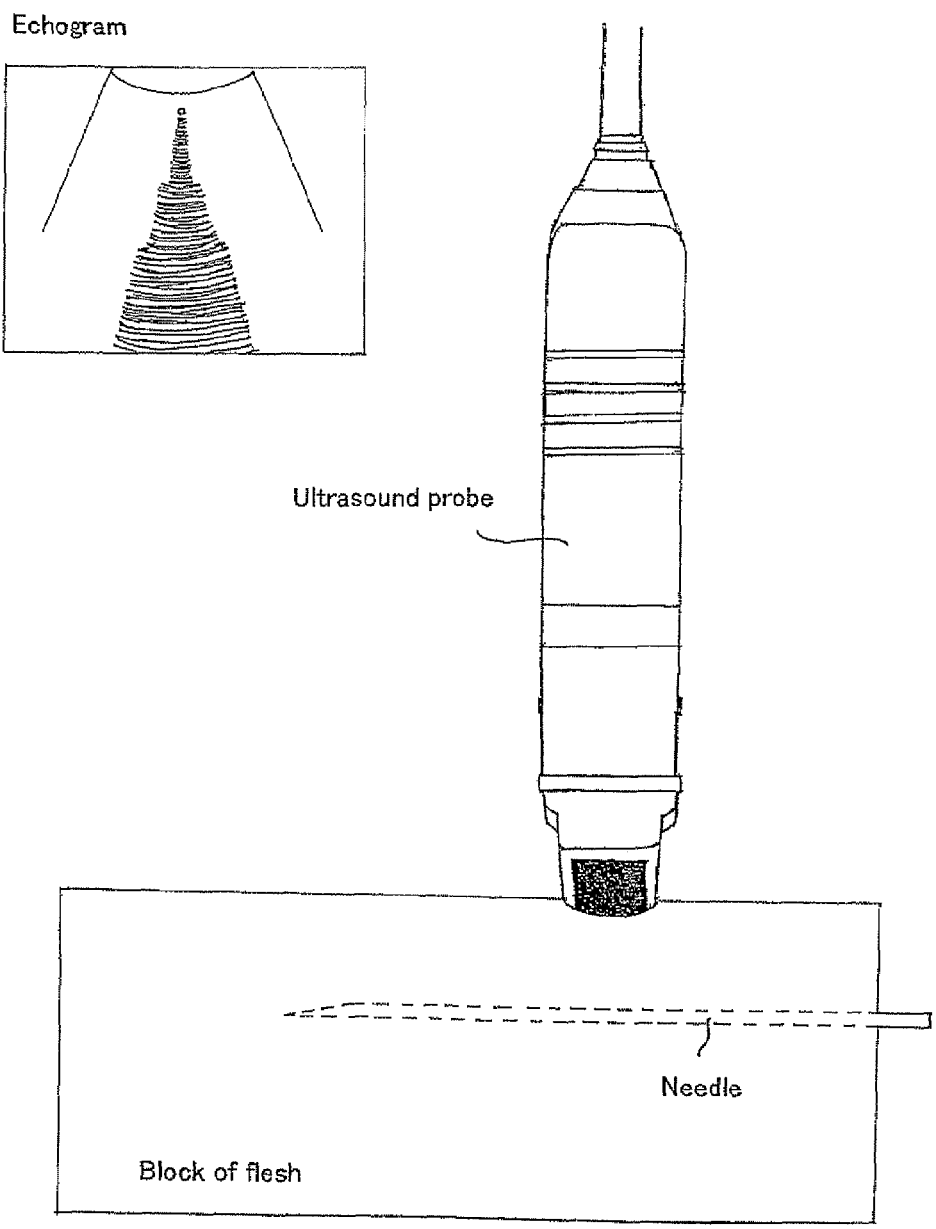
FIG. 1 is a schematic diagram showing a positional relationship between a metal needle and an ultrasound probe when the probe is applied perpendicularly to the needle that is piercing into a block of flesh, and the inset at the upper left is a schematic diagram of an echogram in this case.

In the present invention, the term "metal needle" refers to a metal needle provided with a sharpened edge at the tip thereof. The metal needle may be a hollow metal needle such as an injection needle, or it may be a non-hollow metal needle such as a suture needle. A hollow metal needle has an external shape like a tube with an internal cavity therethrough and is provided with a sharpened edge at the tip portion of the needle. The sharpened edge usually has the shape of a sharp-pointed blade. The hollow metal needle may be a single needle consisting of only a hollow metal needle, or it may be a double-lumen needle in which an inner hollow tube is installed inside a hollow metal needle serving as an outer needle.

Examples of a metal as the material of the metal needle include stainless steel, titanium, nickel-titanium alloy, and magnesium alloy.

The outer diameter and the length of the metal needle, and the inner diameter of the metal needle which is a hollow needle, are set appropriately according to the field of application. For example, a tissue collection needle may usually have an outer diameter of usually 0.5 to 2.5 mm and preferably 1.4 to 1.8 mm, an inner diameter of usually 0.3 to 2.2 mm and preferably 1.0 to 1.6 mm, and a length of usually 50 to 450 mm and preferably 200 to 400 mm. For example, an injection needle may have an outer diameter of usually 0.2 to 3.0 mm and preferably 0.23 to 2.7 mm, an inner diameter of usually 0.05 to 2.9 mm and preferably 0.08 to 2.5 mm, and a length of usually 3 to 200 mm and preferably 4 to 180 mm. A suture needle may have a shape suited to a specific purpose and may have an outer diameter of usually 0.2 to 0.7 mm and preferably 0.3 to 0.6 mm, and a length of usually 3 to 15 mm and preferably 6 to 12 mm.

The above-described metal needle is dipped in a liquid selected from the group consisting of a strong acid solution of a metal, acetic acid, and butyl acetate and then dried; thus, a metal needle that can be imaged in echo imaging is obtained.

Examples of the strong acid include nitric acid, hydrochloric acid, and sulfuric acid. Nitric acid is preferably used in the present invention. For example, the strong acid may be concentrated nitric acid or concentrated sulfuric acid, but the strong acid may usually be used in the form of an aqueous solution. The concentration of the strong acid varies with a metal in the solution and is usually 0.08 to 1.1 mol/L, preferably 0.1 to 1.1 mol/L, more preferably 0.9 to 1.1 mol/L, further preferably 0.92 to 1.08 mol/L, and even more preferably 0.95 to 1.05 mol/L.

In the present invention, the metal in the strong acid solution is preferably a metal selected from the group consisting of a transition element (a d-block element), a lanthanoid, and an actinoid. Examples of such a metal that can be used in the present invention include palladium, gadolinium, germanium, beryllium, strontium, scandium, and samarium. Palladium and gadolinium are preferable, and palladium is more preferable. These metals may be used alone or in a combination of two or more thereof. The concentration of the metal in the strong acid solution of the metal is preferably 900 to 1100 mg/L and more preferably 980 to 1020 mg/L.

Both acetic acid and butyl acetate are liquids. In the present invention, it is not very preferable to use these in the form of an aqueous solution.

In the present invention, the liquid selected from the group consisting of the above-described strong acid solution of a metal, acetic acid, and butyl acetate preferably has a high purity in each case. Examples of such a liquid include a standard stock solution for atomic absorption spectrometry of the above-described metal, acetic acid, or butyl acetate.

The whole or a portion including the needle tip of the above-described metal needle is dipped in the above-described liquid. The dipping conditions are not particularly limited. Usually, dipping is performed at normal temperature (e.g., room temperature) for 10 to 120 minutes, preferably 30 to 60 minutes. During dipping, the liquid may be shaken or stirred.

After dipping, the metal needle is removed from the liquid, washed with water and then dried. The drying temperature is usually 40 to 200° C., preferably 70 to 180° C., and more preferably 100 to 170° C. The drying time is not particularly limited and varies depending on the drying temperature. It is preferable that drying is performed until the metal needle reaches a constant weight. For example, the drying time may be 30 to 60 minutes when the drying temperature is about 70° C. and may be 10 to 30 minutes when the drying temperature is about 150° C.

Figure 2:
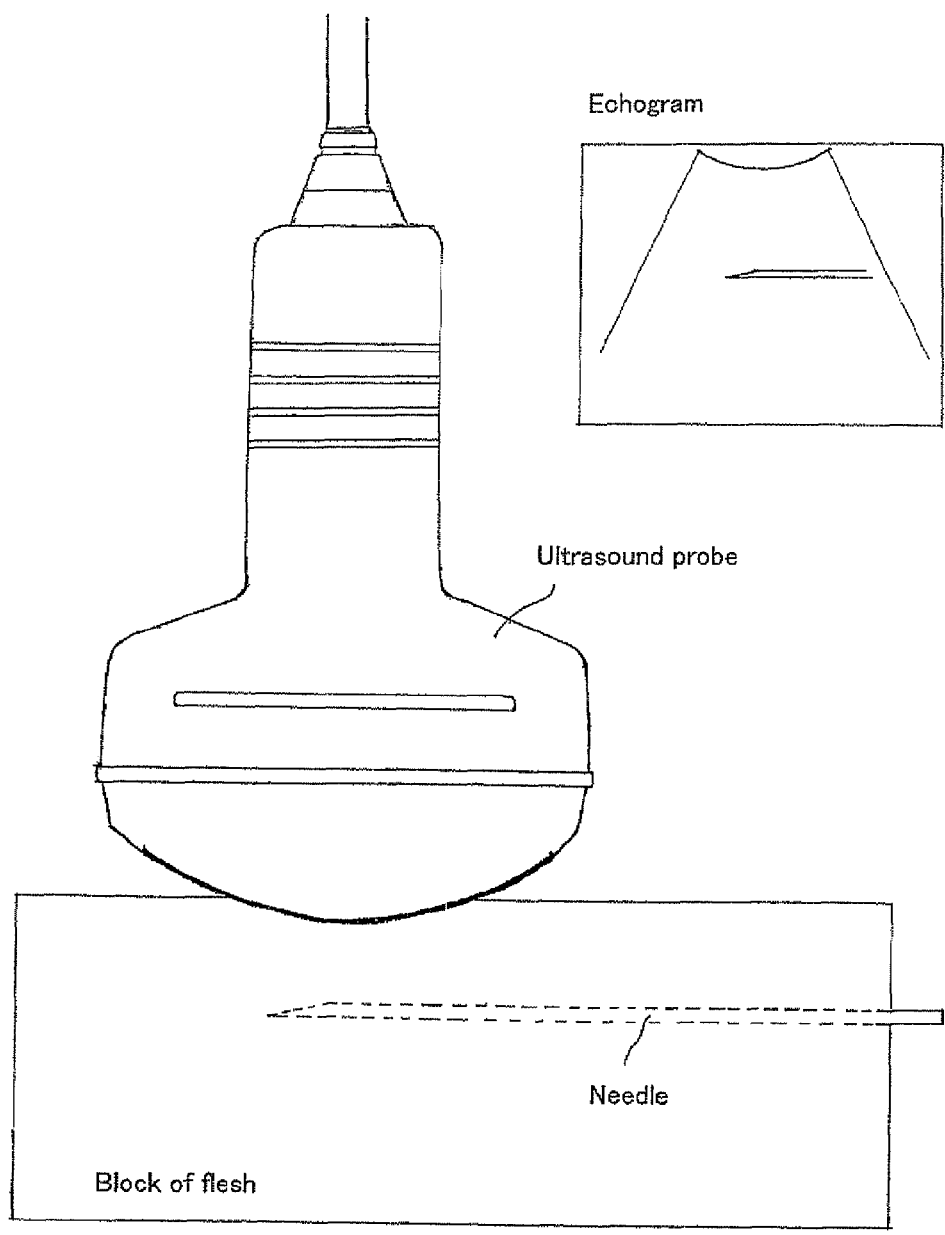
FIG. 2 is a schematic diagram showing a positional relationship between a metal needle and an ultrasound probe when the probe is applied parallel to the needle that is piercing into a block of flesh, and the inset at the upper right is a schematic diagram of an echogram in this case.

The metal needle of the present invention is obtained by being dipped in the liquid and then dried in the above-described manner. The metal needle of the present invention can be imaged in echo imaging when the needle is used to puncture the body, so that the needle can be reliably detected irrespective of the orientation of an ultrasound probe (i.e., a probe that produces ultrasound waves and receives the ultrasound waves (echoes) reflected back) relative to the needle and the scanning direction of the ultrasound probe. For example, as shown in FIG. 1, when the ultrasound probe is applied perpendicularly to the metal needle, the needle is imaged as a point and the shadow of the needle spread from the point in the shape of a sector is clearly projected. Alternatively, as shown in FIG. 2, when the ultrasound probe is applied parallel to the metal needle, the needle is clearly imaged as a line.

Moreover, although the metal needle of the present invention is treated with a strong acid, the needle can also satisfactorily pass a dissolution test and a toxicity test. That is to say, a metal needle that can be used safely and that can be imaged in echo imaging is obtained by only a simple operation, the dipping and drying treatment.

The metal needle of the present invention is preferably used when it is necessary to accurately know the position of a needle inserted into the body as in the case of tissue collection or infusion into a target site. For example, when the metal needle is used for insertion into the body or a body cavity, the needle is useful in confirming insertion of the needle into a blood vessel, confirming arrival of the needle at an organ, and confirming the position of the needle when it is broken. In particular, the metal needle of the present invention is useful as a needle for tissue collection, especially for ovum retrieval from the ovaries.

EXAMPLES

Example 1

Production of Needle Treated with Palladium for 30 Minutes

A hollow needle (having an outer diameter of 1.25 mm, an inner diameter of 0.9 mm, and a length of 150 mm: Kyoshin Co., Ltd.) made of a stainless steel (SUS304) was dipped in 100 mL of a palladium standard stock solution (for atomic absorption spectrometry: Kanto Chemical Co., Inc.) (product specification: palladium 980 to 1020 mg/L; nitric acid 0.9 to 1.1 mol/L) at room temperature for 30 minutes. Then, the needle was removed from the palladium standard stock solution, washed with water, and then dried in a dryer at 150° C. for 15 minutes to give a needle treated with palladium for 30 minutes.

When a dissolution test and a cytotoxicity test were performed on the needle treated with palladium for 30 minutes thus-obtained, there was no particular problem in both tests (data not shown). It should be noted that the dissolution test was performed in accordance with WI Quality and Test Methods of Indwelling Needle for Artificial Kidneys of the Approval Standards for Dialysis-Type Artificial Kidney Apparatus (PAB Notification No. 494 dated Jun. 20, 1983), and the cytotoxicity test was performed in accordance with the Biological Reactivity Tests, IN VITRO (USP 29).

Example 2

Echo Imaging of Needle Treated with Palladium for 30 Minutes-1

Figure 3:
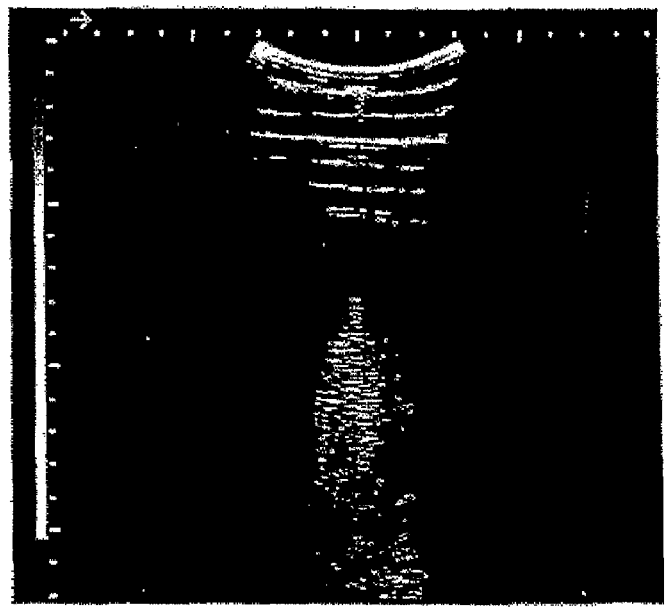
FIG. 3 is a photograph of an echogram taken when an ultrasound probe is applied perpendicularly to a needle that has been treated with palladium for 30 minutes and that is piercing into a block of flesh.
Figure 4:
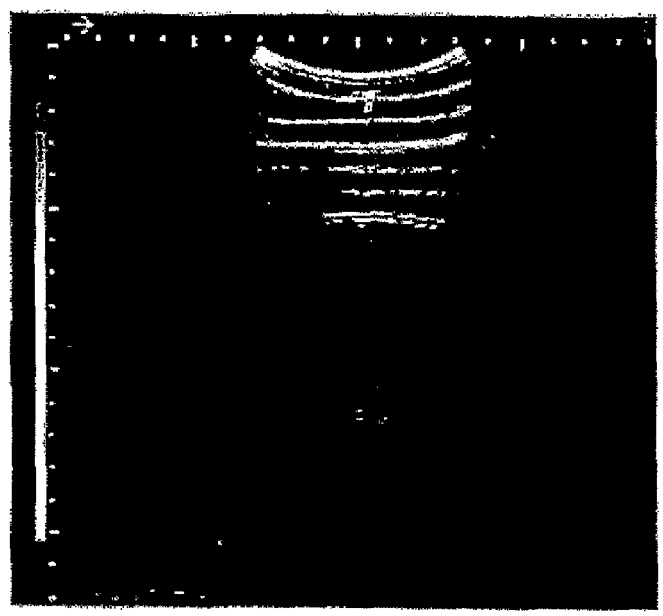
FIG. 4 is a photograph of an echogram taken when an ultrasound probe is applied perpendicularly to a water-treated needle that is piercing into a block of flesh.

The needle treated with palladium for 30 minutes obtained in Example 1 above was used to puncture a block of swine flesh (100 cm×100 cm×100 cm). A probe of a diagnostic ultrasound system (Model No. UF-4500: Fukuda Denshi Co., Ltd.) was placed on the block of flesh so as to be perpendicular to the piercing needle (see FIG. 1), and echo imaging was performed. The results are shown in FIG. 3. It should be noted that imaging was performed in the same manner using, as a control, a water-treated needle obtained by performing the same operation as in Example 1 above except that the palladium standard stock solution was replaced with distilled water. The results are shown in FIG. 4.

As shown in FIG. 3, the needle treated with palladium for 30 minutes was imaged as a point at the upper center of the photograph, and the shadow thereof in the shape of a sector was clearly projected in a lower part of the photograph. In this manner, as for the needle treated with palladium for 30 minutes, the sector shape was clearly detected, and so the position of the pivot of the sector shape could be easily identified as the position of the needle. In contrast, as for the water-treated needle, although the needle seemed to be imaged as a point at the upper center of the photograph as shown in FIG. 4, a sector-shaped shadow was not projected, and so identification of the position of the needle was difficult.

Example 3

Echo Imaging of Needle Treated with Palladium for 30 Minutes-2

Figure 5:
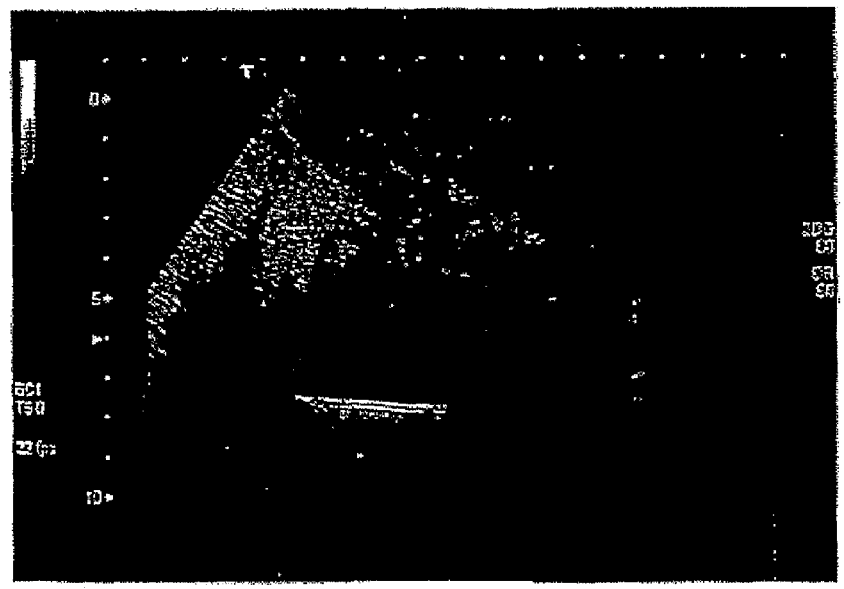
FIG. 5 is a photograph of an echogram taken when an ultrasound probe is applied parallel to a needle that has been treated with palladium for 30 minutes and that is piercing into a block of flesh.
Figure 6:
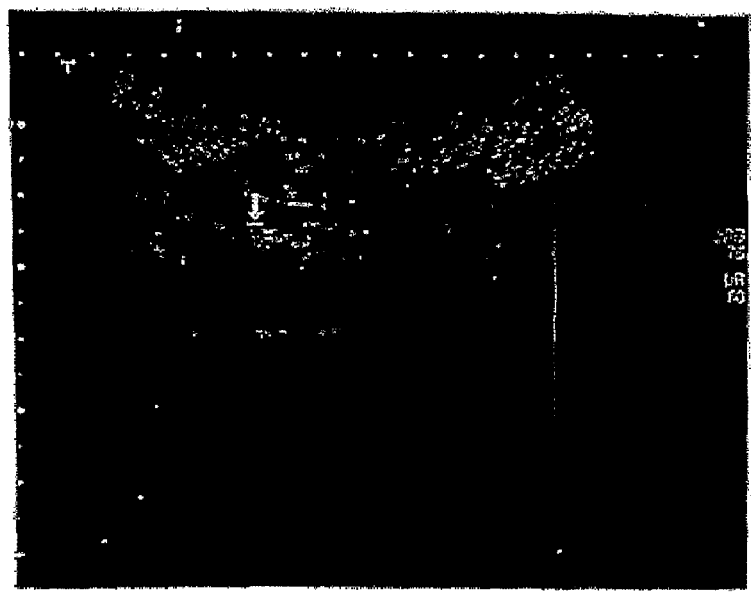
FIG. 6 is a photograph of an echogram taken when an ultrasound probe is applied parallel to a needle that is provided with an echo guide and that is piercing into a block of flesh (conventional art).

The needle treated with palladium for 30 minutes obtained in Example 1 above was used to puncture a block of swine flesh (100 cm×100 cm×100 cm). A probe of a diagnostic ultrasound system (Model No. UF-4500: Fukuda Denshi Co., Ltd.) was placed on the block of flesh so as to be parallel to the piercing needle (see FIG. 2), and echo imaging was performed. The results are shown in FIG. 5. It should be noted that imaging was performed in the same manner using, as a control, a conventional tissue collection needle (having an outer diameter of 0.9 to 1.25 mm, an inner diameter of 0.6 to 0.95 mm, and a length of 400 mm: Cook) provided with an echo guide at the tip of the needle. The results are shown in FIG. 6.

As shown in FIG. 5, as for the needle treated with palladium for 30 minutes, the entire needle was clearly projected. In contrast, as for the conventional needle provided with the echo guide at the tip thereof, only the tip portion of the needle was projected, as shown by the white arrow in FIG. 6, and so it was not easy to find the image of the needle at rest.

Example 4

Examination of Treatment with Various Liquids

Needles treated with various liquids were produced by performing the same operation as in Example 1 above except that the palladium standard stock solution was replaced with the liquids listed in Table 1 below. It should be noted that all of the standard stock solutions or the standard solutions of the metals listed in Table 1 were nitric acid solutions. Then, echo imaging was performed in the same manner as in Example 3 above on each of the liquid-treated needles thus-obtained. The results are collectively shown in Table 1.

TABLE 1

| Liquids[*1] | Imaging results[*2] |
|---|---|
| Gadolinium standard stock solution (for atomic absorption spectrometry) | + |
| Germanium standard stock solution (for atomic absorption spectrometry) | + |
| Beryllium standard stock solution (for atomic absorption spectrometry) | + |
| Strontium standard solution (for chemical analysis) | + |
| Scandium standard stock solution (for atomic absorption spectrometry) | + |
| Samarium standard stock solution (for atomic absorption spectrometry) | + |
| Butyl acetate (for atomic absorption spectrometry) | + |
| Acetic acid (for atomic absorption spectrometry) | + |

[*1]All of the liquids were purchased from Kanto Chemical Co., Inc.
[*2]"+" indicates that the needle could be imaged.

As a result of treatment with the various liquids listed in Table 1, all of the stainless-steel needles were imaged well.

According to the present invention, a metal needle that can be easily imaged even with a general-purpose ultrasound imaging system is provided. This metal needle can be obtained by a very simple treatment and also presents no safety problems. Therefore, the needle of the present invention is useful when it is necessary to accurately know the position of a needle inserted into the body as in the case of tissue collection or infusion into a target site. Furthermore, it is also possible to detect the position of, for example, an indwelling needle in the body or a needle left in the body during surgery.

The invention claimed is:

1. A method of obtaining a metal needle that is visible in echo imaging, the method comprising the steps of: dipping the metal needle in a strong acid solution of a metal, and drying the needle, wherein the strong acid solution of a metal is a nitric acid solution of a metal selected from the group consisting of a transition element, a lanthanoid, and an actinoid.

2. The method of claim 1, wherein the strong acid solution of a metal is a nitric acid solution of a metal selected from the group consisting of palladium, gadolinium, germanium, beryllium, strontium, scandium, and samarium.

3. The method of claim 2, wherein the strong acid solution of a metal has a concentration of the metal of 980 to 1020 mg/L and a concentration of the strong acid of 0.08 to 1.1 mol/L.

4. The method of claim 2, wherein the metal needle is for tissue collection.

5. The method of claim 2, wherein the solution is a standard stock solution for atomic absorption spectrometry.

6. The method of claim 1, wherein the strong acid solution of a metal has a concentration of the metal of 980 to 1020 mg/L and a concentration of the strong acid of 0.08 to 1.1 mol/L.

7. The method of claim 6, wherein the metal needle is for tissue collection.

8. The method of claim 6, wherein the solution is a standard stock solution for atomic absorption spectrometry.

9. The method of claim 1, wherein the metal needle is for tissue collection.

10. The method of claim 9, wherein the solution is a standard stock solution for atomic absorption spectrometry.

11. The method of claim 1, wherein the solution is a standard stock solution for atomic absorption spectrometry.

* * * * *